United States Patent [19]
Bokros

[11] Patent Number: 4,692,165
[45] Date of Patent: Sep. 8, 1987

[54] HEART VALVE

[75] Inventor: Jack C. Bokros, Austin, Tex.

[73] Assignee: CarboMedics, Inc., Austin, Tex.

[21] Appl. No.: 806,032

[22] Filed: Dec. 6, 1985

Related U.S. Application Data

[63] Continuation-in-part of Ser. No. 653,960, Sep. 24, 1984, abandoned.

[51] Int. Cl.⁴ .............................................. A61F 2/24
[52] U.S. Cl. ......................................................... 623/2
[58] Field of Search ............................................ 623/2

[56] References Cited
U.S. PATENT DOCUMENTS

| | | | |
|---|---|---|---|
| 4,306,319 | 12/1981 | Kaster | 623/2 |
| 4,373,216 | 2/1983 | Klawitter | 623/2 |
| 4,535,484 | 8/1985 | Marconi | 623/2 |

Primary Examiner—Richard J. Apley
Assistant Examiner—Alan W. Cannon
Attorney, Agent, or Firm—Fitch, Even, Tabin & Flannery

[57] ABSTRACT

Improved versions of heart valve prostheses include the usual generally annular body having an interior surface defining a blood flow passageway and having one or two occluders supported thereon for alternately blocking and then allowing the flow of blood in a predetermined direction. Notches are formed at opposite locations in the periphery of an occluder, and each is disposed about a pivot post that projects radially inward from the interior surface of the annular body. A pair of stops flank each pivot post, having curved surfaces at locations adjacent to the pivot posts but radially inward from the ends thereof that function as oppositely disposed fulcrums and cooperate with the pivot posts in defining the opening and closing movement of each occluder. Preferably, the pivot posts and the stop means are formed as an integral structure. Self-centering seats can be used to provide a better seal in the closed position.

15 Claims, 30 Drawing Figures

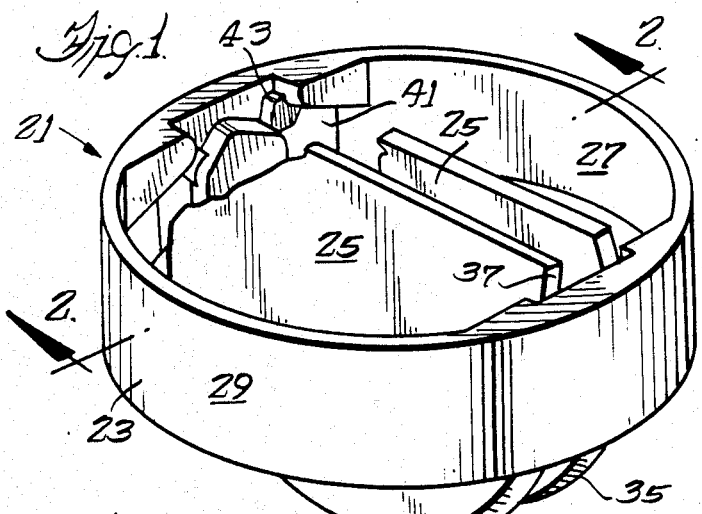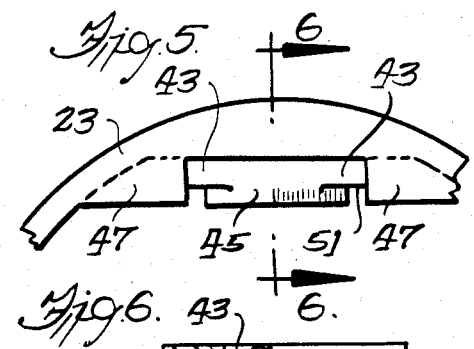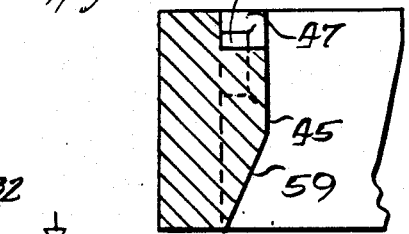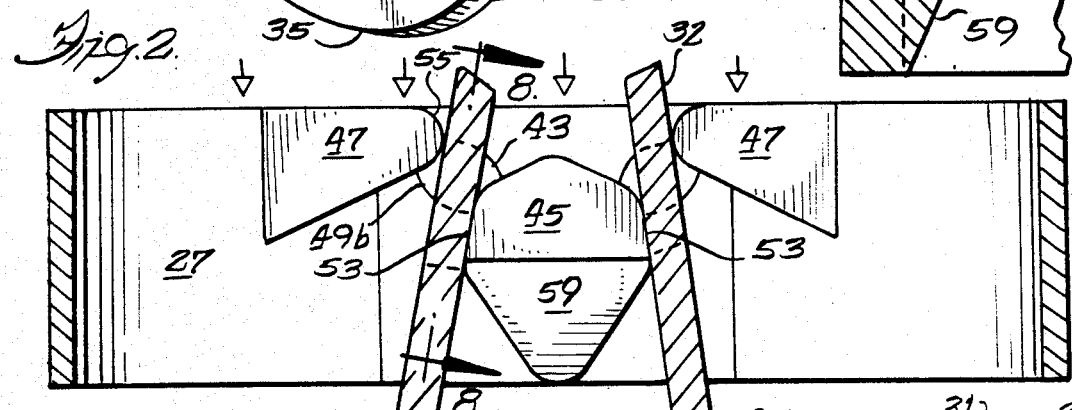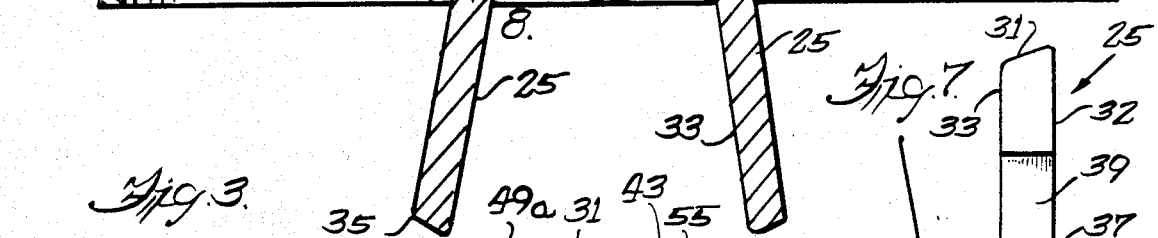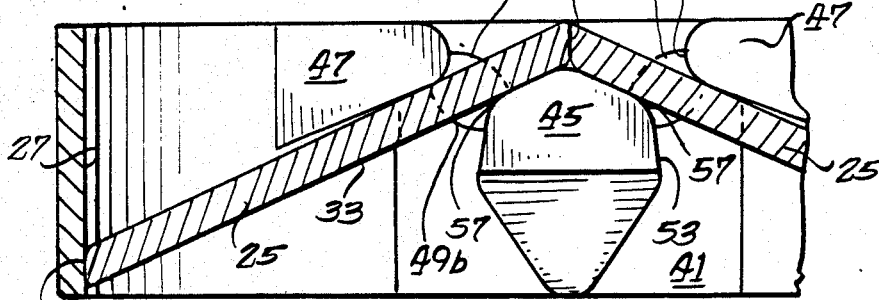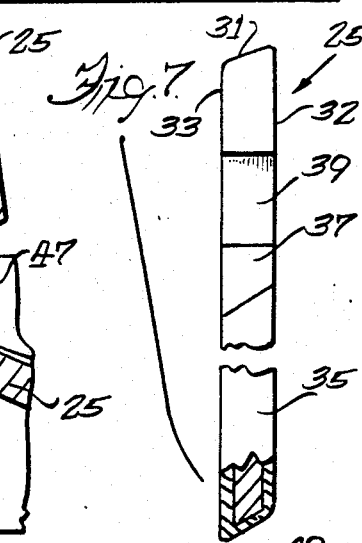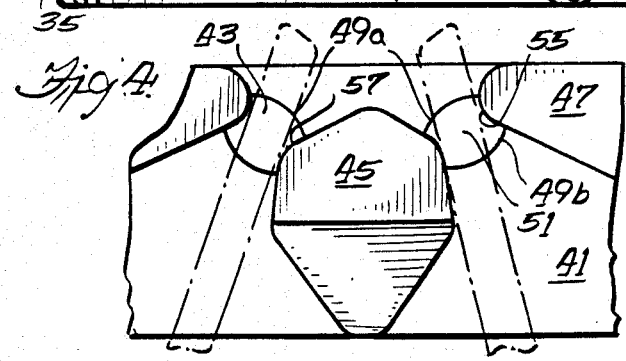

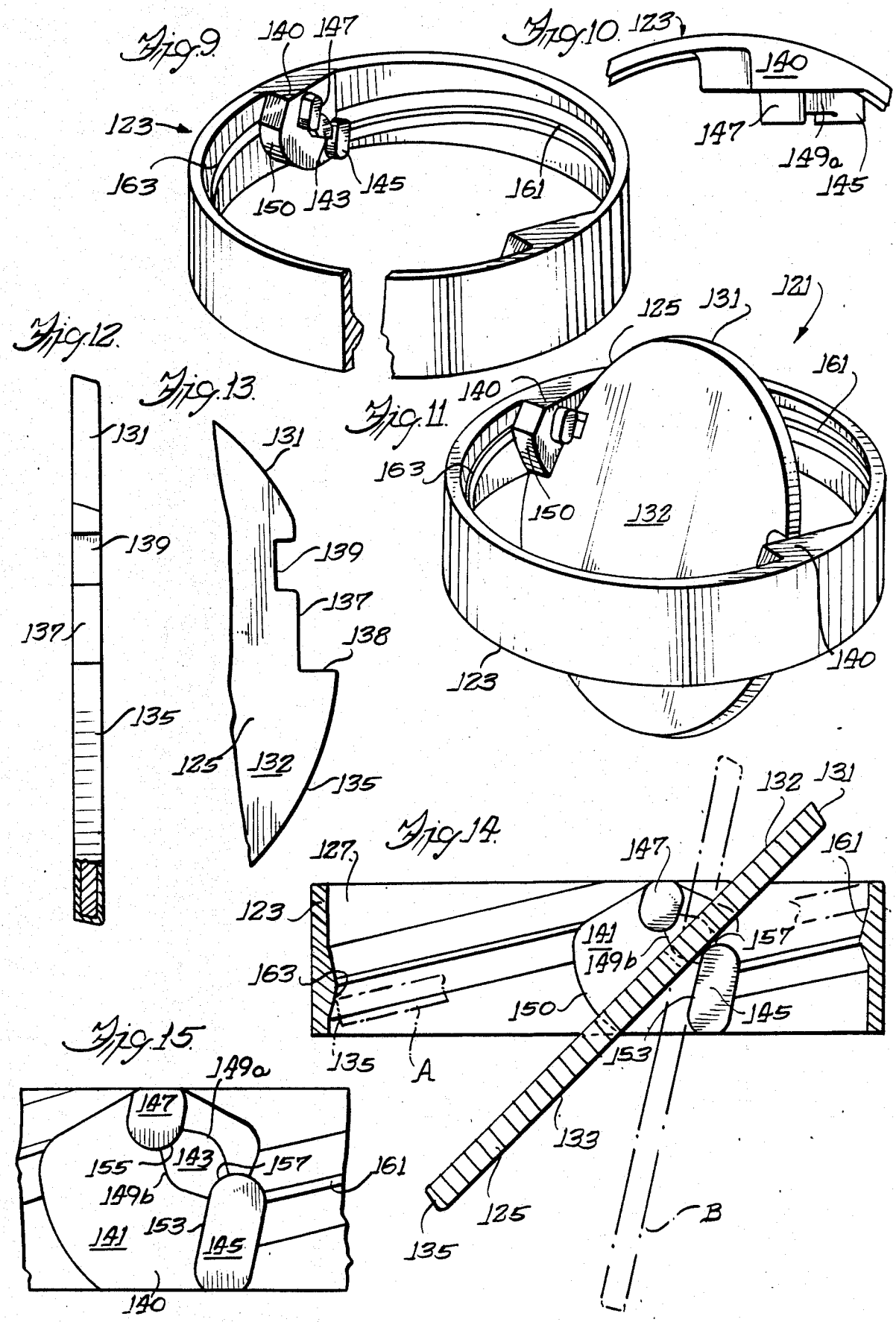

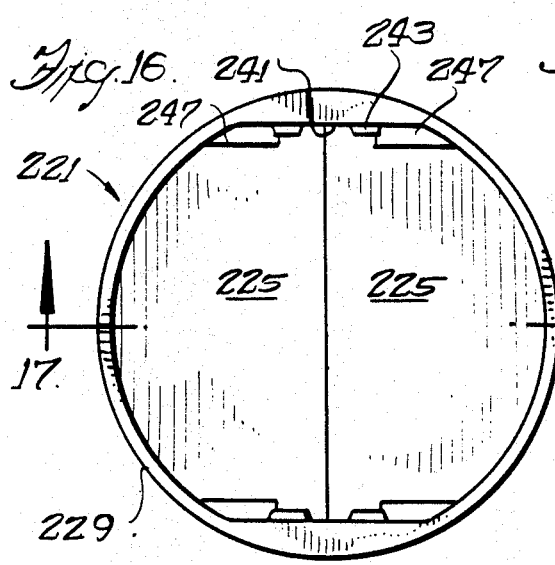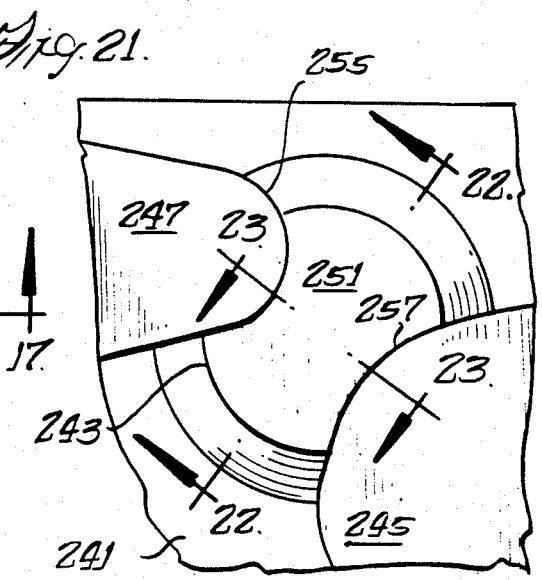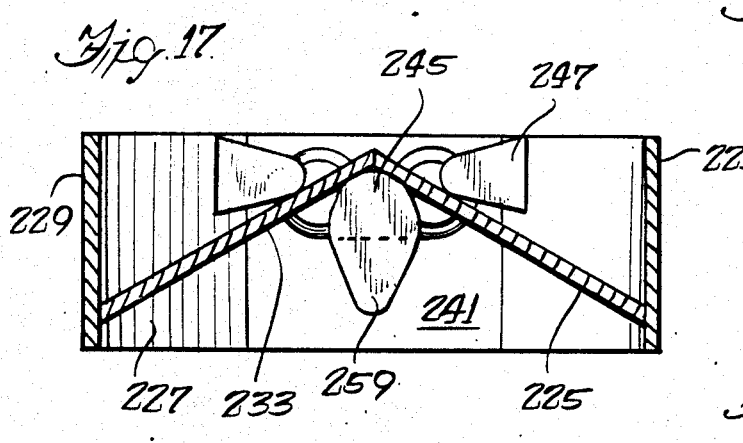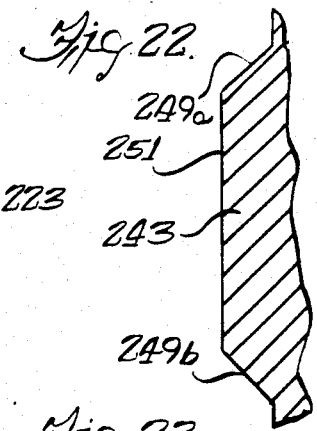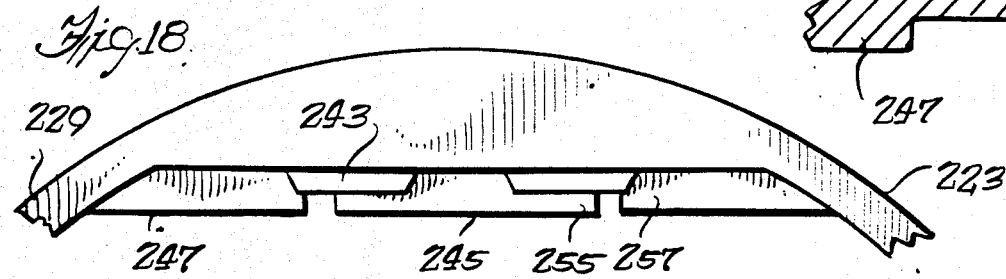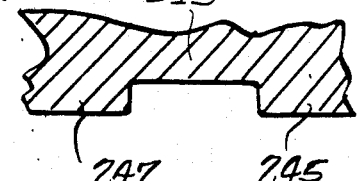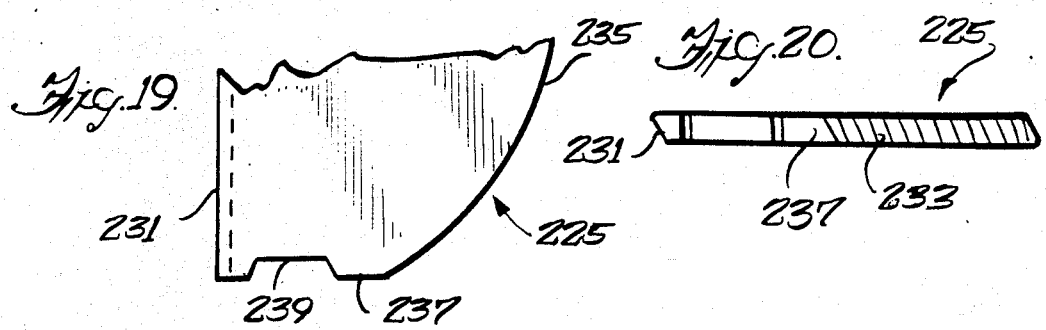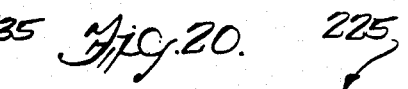

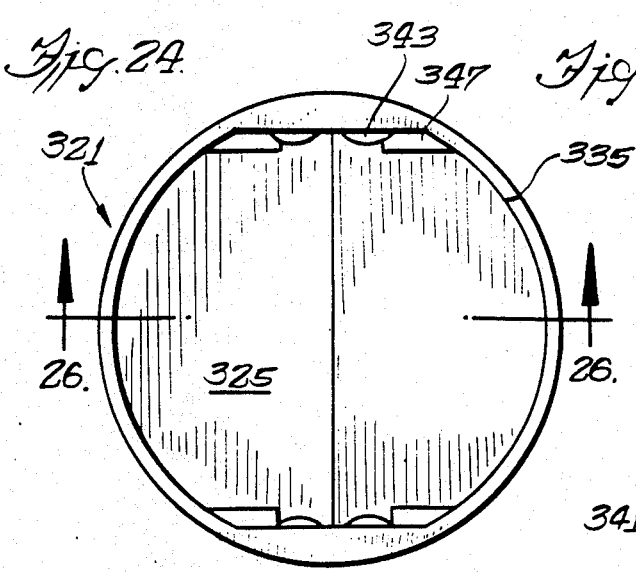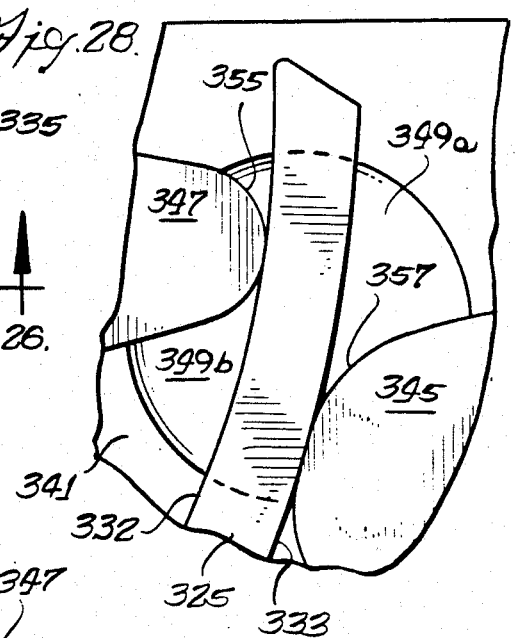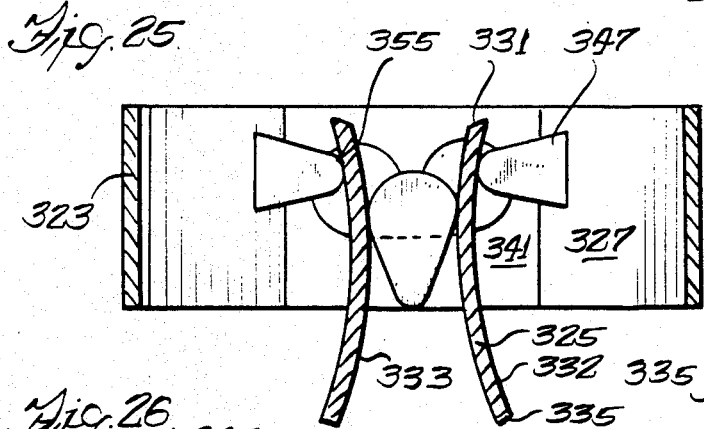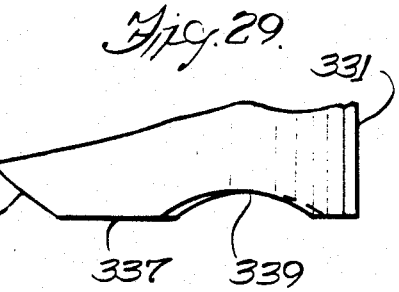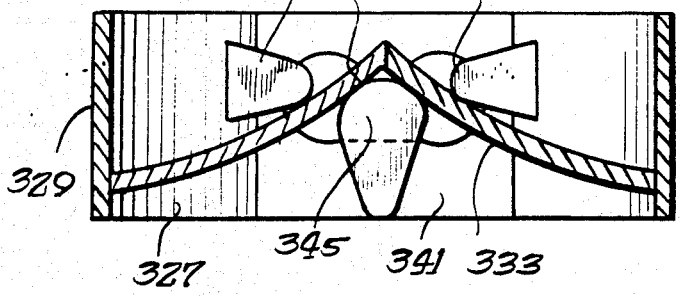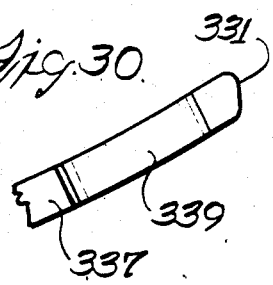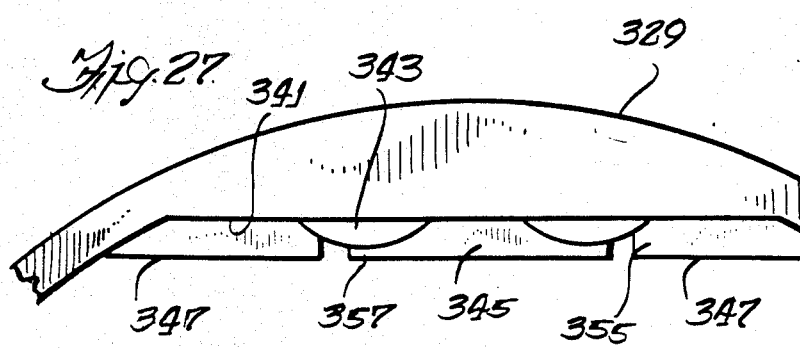

HEART VALVE

This application is a continuation-in-part of my earlier application Ser. No. 653,960, filed Sept. 24, 1984, abandoned 9/17/86.

This invention relates to heart valve prostheses for replacement of defective natural valves and more particularly to heart valve prostheses which employ one or more occluders in the form of flat platelike members, although certain features of the invention are applicable to valves having curved occluders.

BACKGROUND OF THE INVENTION

Various types of heart valve prostheses have been developed which operate hemodynamically as a result of the pumping action of the heart and which are in essence functioning as check valves. Early heart valves employed a ball-and-cage arrangement whereas later versions of heart prostheses have employed one or more occluders generally in the form of a plate or disc which might be flat or of a curved shape. Bokros U.S. Pat. No. 3,546,711 shows a heart valve having a circular occluder which is pivoted from a hinge pin that coacts with a pair of upstanding fins located on the downstream surface of the occluder. Bokros U.S. Pat. No. 4,178,639 shows a bi-leaflet heart valve having a pair of platelike members each of which has ears extending from its opposite lateral edges that pivot in spheroidal guides located in the orifice ring. U.S. Pat. No. 3,445,863 shows a heart valve arrangement having one or more occluders in the form of flat plates having cut-outs at their edges which are proportioned to interfit with complementary cut-outs in a base ring formed of generally similar material. U.S. Pat. No. 4,225,980 shows a metallic heart valve which includes an oval-shaped occluder having cut-outs in opposite lateral edges which coact with parabolic pivots or pegs that extend radially inward from the interior surface of the orifice ring. U.S. Pat. No. 4,078,268 shows a bi-leaflet valve having a pair of semicircular occluders which have ears extending upward from the downstream surface thereof that co-act with fulcrums to effect a pivoting action. U.S. Pat. No. 4,159,543 shows a variety of bi-leaflet valves, one version of which has grooves cut into the edges of the semicircular occluders at an oblique angle to the surface thereof, which grooves receive generally conical pivot pins that extend radially inward from the interior surface of the orifice ring. U.S. Pat. No. 4,373,216 illustrates heart valves having one or more occluders that have notches in opposite edges of the periphery thereof which co-act with elongated protuberances extending inward from the surface of the orifice ring and providing tracks for guiding pivotal and translational movement of the occluders.

As is apparent from the foregoing, a wide variety of different heart valves have been designed, and work continues on new heart valve designs in order to still farther improve the functioning of these prostheses which are being used in greater quantity each year as surgical techniques improve throughout the world.

SUMMARY OF THE INVENTION

The invention provides improved versions of heart valve prostheses which each include the usual generally annular body having an interior surface defining the central blood flow passageway along with one or more occluders supported thereon for alternately blocking and allowing the flow of blood in a predetermined direction, in generally check-valve fashion. Formed at opposite locations in the periphery of an occluder is notch means which may be generally rectangular in shape, each of which receives a pivot post that projects radially inward from the interior surface of the annular body. In flanking locations to each pivot post are a pair of stop means that present curved surfaces in the regions adjacent to the pivot posts at locations radially inward from the ends of the pivot posts. These curved surfaces function as oppositely disposed fulcrums that cooperate with the pivot posts in defining the opening and closing movement of the occluder. Preferably, the pivot posts and the stop means are formed as an integral structure so as to avoid any gap therebetween which would provide a stagnant region where blood clotting might occur.

BRIEF DESCRIPTION OF THE DRAWINGS

FIG. 1 is a perspective view of a bi-leaflet heart valve embodying various features of the invention, shown in the open position.

FIG. 2 is an enlarged sectional view taken generally along the line 2—2 of FIG. 1.

FIG. 3 is a fragmentary view similar to FIG. 2 showing the leaflets in the closed position.

FIG. 4 is a fragmentary view, similar to FIGS. 2 and 3, of the orifice ring with the leaflets being shown in broken lines in an approximate position they might assume during opening movement.

FIG. 5 is a fragmentary plan of the orifice ring shown in FIG. 4.

FIG. 6 is a fragmentary sectional view taken along line 6—6 of FIG. 5.

FIG. 7 is a side view of one of the occluder leaflets with portions broken away to illustrate its interior structure.

FIG. 8 is a fragmentary sectional view taken generally along the line 8—8 of FIG. 2.

FIG. 9 is a perspective view of an alternative embodiment of an annular body suitable for use as a part of a single-occluder heart valve.

FIG. 10 is a fragmentary plan view of the annular body shown in FIG. 9.

FIG. 11 is a perspective view of the heart valve showing the annular body of FIG. 9 with the occluder installed and in the open position.

FIG. 12 is a side view of the occluder with a portion broken away to show its internal construction.

FIG. 13 is a fragmentary front view of the occluder.

FIG. 14 is a sectional view of the heart valve shown in FIG. 11 depicting in full lines the occluder in an intermediate position as it is moving to the closed position and with the occluder shown twice in broken line in the position which it assumes in the open position and in the closed position.

FIG. 15 is an enlarged fragmentary view of the interior surface of the annular ring emphasizing the pivot support area.

FIG. 16 is a plan view of an alternative design bi-leaflet heart valve embodying various features of the invention, shown in the closed position.

FIG. 17 is an enlarged sectional view taken generally along the line 17—17 of FIG. 16.

FIG. 18 is an enlarged fragmentary plan view of the orifice ring shown in FIG. 16.

FIG. 19 is a fragmentary view of a leaflet.

FIG. 20 is a side view of an occluder leaflet.

FIG. 21 is a fragmentary view, similar to FIG. 17, of the orifice ring with the leaflets removed greatly enlarged in size.

FIG. 22 is a fragmentary sectional view taken along line 22—22 of FIG. 21.

FIG. 23 is a fragmentary sectional view taken generally along the line 23—23 of FIG. 21.

FIG. 24 is a perspective view of another alternative embodiment of a bi-leaflet heart valve.

FIG. 25 is a side view of the heart valve of FIG. 24 with the occluders in the open position.

FIG. 26 is a side view of the heart valve with the occluders in the closed position.

FIG. 27 is a fragmentary plan view of the annular body shown in FIG. 24 enlarged in size and with the leaflets removed.

FIG. 28 is a fragmentary view, similar to FIG. 17, of the orifice ring and one leaflet greatly enlarged in size.

FIG. 29 is a fragmentary plan view of one of the leaflets.

FIG. 30 is a side view of an occluder leaflet.

DETAILED DESCRIPTION OF THE PREFERRED EMBODIMENTS

Illustrated in FIG. 1 is a heart valve 21 which consists of an annular valve body or housing 23 which supports a pair of pivoting lealets or occluders 25 that open and close to control the blood flow through a central passageway or orifice which is defined by the interior surface 27 of the valve body. Inasmuch as the annular body 23 defines the central passageway or orifice, it is sometimes referred to as an orifice-ring. The normal flow of blood through the heart valve 21 is downward in the orientation in which the valve is shown in FIGS. 1 and 2, as represented by the small arrows which appear at the top of FIG. 2. It should, of course, be understood that the valve 21 can operate in any orientation and is not significantly affected by gravity. Thus, the terms such as upward and downward, as used hereinafter, are merely employed to facilitate explanation and understanding and are not meant to place any limitations upon the operation of the heart valves being described.

As depicted, the annular body 23 has a smooth exterior surface 29 which is that of the lateral surface of a right circular cylinder. It should be understood that suitable means, such as a peripheral groove or a pair of flats, would usually be provided for attaching a suturing ring to the annular body to facilitate sewing or suturing of the heart valve 21 to the heart tissue. However, inasmuch as the suturing ring and its means of attachment to the heart valve 21 form no part of the present invention, it is simply omitted so as to facilitate the illustration of the specific components of the heart valve with which the invention is concerned. U.S. Pat. No. 4,233,690, issued Nov. 18, 1980, illustrates one method of attaching a suturing ring to an annular heart valve body, and the disclosure of this patent is incorporated herein by reference.

The valve body 23 and the leaflets 25 may be made of any suitable material that is biocompatible and non-thrombogenic and that will take the wear to which it will be subjected during countless opening and closing movements of the leaflets. Preferably, the leaflets are made of isotropic graphite, such as that sold under the tradename POCO and that preferably contains between about 5 and about 20 weight percent tungsten to render it radio-opaque and allow x-ray visualization, which graphite has been suitably coated with pyrolytic carbon, such as that sold under the trademark PYROLITE. The lower portion of FIG. 7 shows the pyrocarbon coating on the graphite substrate. Such pyrocarbon gives excellent blood and tissue compatibility and wear-resistance.

The orifice ring 23 can be made in the same fashion using a pyrocarbon-coated substrate, or it can be, and preferably is, made from solid PYROLITE pyrocarbon. A preferred process for forming an orifice ring from all pyrocarbon by coating a mandrel, which is subsequently removed, is disclosed in European Patent Application, Publication No. 0055406 Al, the disclosure of which is incorporated herein by reference.

The illustrated leaflets 25 are flat and have a uniform thickness throughout. Each leaflet 25 has a straight-edge portion 31, which is best seen in FIG. 7 and which is oriented at an angle to the downstream surface 33 of the leaflet so that the two straight-edge portions 31 abut in substantially face-to-face contact when the pair of leaflets are in the closed position as depicted in FIG. 3. Generally, the angle will be between about 110° and about 130°, being of course dependent upon the orientation of the leaflets to the horizontal or transverse plane in the closed position, as depicted in FIG. 3. In addition, each of the leaflets 25 has a major arcuate, nearly semicircular, edge 35 (see FIG. 1) and a pair of intermediate or transitional straight edge portions 37 which are flat and perpendicular to the upstream and downstream surfaces of the leaflets. In addition, each leaflet 25 contains a pair of notches 39 disposed in its opposite lateral edges in the regions of the straight edge surfaces 37. As best seen in FIG. 8, the notches are generally rectangular in shape, and all of the defining edges are rounded as opposed to being sharp.

The passageway-defining interior surface 27 of the annular body 23 also has a right circular cylindrical shape for a major portion of its length but is interrupted by a pair of diametrically opposed flat sections 41 from which the support means for holding and defining the movement of the leaflets 25 radially project. The support means includes a pair of pivot posts 43, which are sized to fit within the notches 39 and which pivot posts are flanked by stop means 45, 47. As can be seen from FIGS. 1 and 5, the flanking stop means 45, 47 project radially farther inward than do the pivot posts 43. Preferably, the pivot posts 43 and the flanking stop means are formed integrally with one another, and most preferably this overall support structure is formed as an integral part of the annular body 23, as by machining a pre-shaped body of pyrolytic carbon to final dimensions. As best seen in FIG. 4, the pivot posts 43 each have a pair of opposite arcuate surfaces, a generally upper surface 49a and a generally lower surface 49b, which are referred to as the lateral surfaces of the posts 43, so as to be distinguished from the flat end surface 51 of each pivot post.

The leaflets 25 are suitably assembled with the annular ring 23 by suitably distorting the ring, as by squeezing the ring inward at its relatively thin, hollow, cylindrical regions so that the diametrically opposite, thicker regions where the flat surfaces 41 are located move away from each other sufficiently far to allow the insertion of the notched leaflets. Instead of squeezing, the thicker portions may be pulled outward. An all PYROLITE pyrocarbon annular body 23 has sufficient resiliency to permit this distention and to return to its originally machined configuration. In the assembled heart valve, the depth of the notch 39 is slightly greater than the length of the pivot post 43 so that one of the lateral edge surfaces 37 of the leaflet will bear against a facing flat section 41 of the annular body, as illustrated in FIG. 8.

In the open position depicted in FIG. 2, the leaflets 25 lie at an angle of about 5° to 15° to the centerline of the valve passageway with the upper edge surface of the notch 39 in contact with the arcuate surface 49a of the pivot post 43, see also FIG. 8. The orientation of the leaflet is maintained and defined generally by contact of the downstream surface 33 of the leaflet against side surfaces 53 formed on the central stop 45. In addition, there will be line contact between the upstream surface 32 of the leaflets 25 and an arcuate surface 55 which is formed on the stops 47 in a location that is intermediate of the upstream surface 49a and the downstream surface 49b of the pivot post 43 and is spaced radially inward thereof.

When the downstream (downward as depicted in FIG. 2) flow of blood is discontinued as the contraction of the respective ventricle terminates with respect to an aortic valve, the respective ventricle will then begin to relax in order to draw more blood into the chamber from the atrium, and as a result the back pressure which is present within the aorta causes blood to tend to flow upstream (upward, as illustrated in FIGS. 2 and 3) causing the leaflets 25 to swing or pivot toward the closed position. The leaflets are quickly displaced slightly upward so that the lower surfaces of the rectangular notches 39 bear against the arcuated surfaces 49b of the pivot posts, and the swinging of the leaflets is guided by contact at these points, together with contact between the upstream surface 32 of the leaflets 25 and the arcuate surface 55 on the stops 47.

When the closed position is reached as depicted in FIG. 3, the arcuate edges 35 of the leaflets 25 lie in contact with the interior surface 27 of the annular body. Accordingly, the shape of the arcuate edge 35 will generally be that of a section of an ellipse, i.e., the intersection between a plane and a right circular cylinder, and the edge is preferably bevelled as shown (FIG. 7) so as to more closely seat against the interior cylindrical surface. In addition, there may be line contact between the arcuate surface 55 of the stops 47 and the upstream surface 32 of the leaflets, and the straight-edge portions 31 of the two leaflets 25 will also abut in substantially face-to-face contact, all as shown in FIG. 3. There possibly may also be some slight touching between the downstream surface 33 of the leaflets 25 and region of a pair of curved surfaces 57 which are formed on the central stop 45 at locations just above the side surfaces 53 and which thus lie intermediate of the upstream and downstream arcuate surfaces 49a,b and radially inward of the pivot posts.

When the pumping stroke again occurs, the pressure against the upstream surface of the leaflets 25 immediately displaces the leaflets downward against the central stop 45, and pivoting begins guided by the line contact between the undersurface 33 of the leaflets 25 and the curved surfaces 57, as depicted in ghost outline in FIG. 4. In addition, the leaflets will be displaced slightly so that there is contact between the upper surfaces of the notches 39 and the arcuate surfaces 49a on the pivot posts.

By forming the posts 43 and stop means 45, 47 integral with one another, the regions of joinder can be blended together arcuately so there are no sharp depressions or valleys, i.e. no regions of concave curvature having a radius of curvature less than about 0.2 mm., which would be locations ripe for the beginning of clotting; thus, there is a substantial advantage gained from being able to have such a smooth transition from surface-to-surface, particularly where the very ends of the arcuate surfaces are not necessary for guidance. Moreover, the desired smooth swinging of the leaflets between the open and closed positions is farther facilitated by the radius of curvature which appears on the surfaces 49a and 49b of the pivot posts 43. In this respect, the focal point of the radius of curvature of each of these surfaces 49a, 49b should lie beyond the center point of the pivot post and may even lie past the opposite side of the pivot post. By examining the leaflets in the closed position as shown in FIG. 3, it will be seen that this arrangement between the arcuate surface 49a and the substantially flat surfaces defining the upper end of the notch 39 creates an immediate sharp pivoting movement which tends to more quickly open the valve in response to the beginning of the pumping stroke. In addition to blending the transition areas between adjacent surfaces, streamlining is also provided as by creating an oblique undersurface 59 on the central stop 45.

In summary, the integral pivot post and stop arrangement minimizes interference with blood flow, while at the same time providing for effective washing of the surfaces to avoid clotting; moreover, very effective and positive control of the swinging of the leaflets is provided as a result of the short pivot posts 43 which are flanked by the stop means which protrude farther radially inward into the passageway and thereby serve not only as stop surfaces, but also fulcrums to assist the pivoting movement. As best seen perhaps by examining FIGS. 4 and 8 together, the movement of the leaflet about the surface 49a as a fulcrum is primarily a rolling action, with a minimum of sliding movement, which is important to reduce wear in a device such as this that must continue to operate satisfactorily for an indeterminate number of years. The ability to blend the pivot posts into the stop means, which results from the integral nature of them, allows the design to take advantage of the contact between the pivot post and the stop means which provides overall strengthening of the structure without having to suffer the disadvantage of precisely matching individually machined components to try to avoid minor crevices and valleys that might likely promote the formation of blood clotting.

Depicted in FIGS. 9–15 of the drawings is an alternative embodiment of a heart valve 121 which includes an annular body 123 designed to operate with a singular flat occluder or disc 125. Generally, the same principles of design are executed in the heart valve 121 as were hereinbefore explained in detail with respect to the bi-leaflet valve 21, and therefore similar numbers in the 100 series are utilized to refer to comparable components. Moreover, it should be understood that, unless specifically stated hereinafter, the function and construction of the comparable components will be essentially the same as previously described.

The annular body 123 has an interior surface 127 which defines the passage or orifice through which the bloodstream will flow and is illustrated with a smooth exterior cylindrical surface 129 for the reason set forth hereinbefore. The interior surface 127 does differ from that of the bi-leaflet version in that, as described in detail hereinafter, inwardly extending lands 161, 163 are provided against which the arcuate edges of the disc occluder 125 can positively seat.

The occluder 125 generally has the form of a flat disc having an upstream surface 132 and a downstream surface 133. The periphery of the disc includes a minor arcuate section 131, a major arcuate section 135 and a pair of oppositely disposed, straight, parallel intermediate sections 137. Notches 139 of generally rectangular shape are located in the regions of the straight edge portions 137. The shape of the major arcuate edge 135 is generally that of a section of an ellipse, and the shape of the minor arcuate edge section 131 is also generally that of a section of an ellipse with a slightly shorter minor axis. As best seen perhaps in FIG. 13, the intermediate edge portions are each inwardly offset from the outermost lateral extension of the major edge surface by short perpendicular transitional surfaces 138 that are collinear. As best seen in FIG. 12, the circular disc is also preferably made of isotropic graphite which has been coated with PYROLITE pyrolitic carbon.

The pivot and stop means arrangement is also preferably formed integrally as a part of the annular body 123 for the reasons as hereinbefore described with regard to the annular body 23 illustrated in FIGS. 1 through 8; however, the design of the arrangement differs somewhat because of the single occluder concept. Instead of forming a pair of opposed flat regions at opposite locations within an otherwise annular body having an interior passageway of generally circular cross section, improved guidance of the occluder is obtained by providing a pair of protrusions or lands 140 which extend from the inner surfaces of the annular body 123 and present a pair of oppositely disposed flat surfaces 141. The protrusions 140 lie substantially to to the right of a diameter of the passageway which is parallel to the pivot axis as viewed in FIG. 14.

Projecting radially inwardly from each of these flat surfaces 141 is a pivot post 143 and a pair of stops 145, 147. The pivot posts 143 have arcuate, generally upper and lower surfaces 149a, b which are similarly formed with the focal point of the radius of curvature lying beyond the center point of the pivot post and, if desired, past the opposite surface of the post, for the purpose described hereinbefore.

The annular body 121 is suitably distended, as described hereinbefore, so as to allow the occluder 125 to be snapped into place with the notches 139 fitting above the pivot posts 143. As described previously, the length of the pivot post 143 is just less than the depth of the notches 139 so that the flat edge surfaces 137 of the occluder will bear against the flat surface 141 of the protrusions and provide a bearing surface during pivoting between open and closed positions. In addition, each protrusion 140 is formed with a curved undersurface 150 against which the transitional surface 138 wipes during pivoting action.

In the open position, as shown in FIG. 11 and in broken lines in FIG. 14, the occluder is oriented at between about 5° and 15° to the centerline of the passageway, e.g., at about 10°, lying generally against an inward-facing surface 153 of the stop 145 and with the upper surface of the notch 139 in contact with the upper surface 149a of the pivot post. There may also be contact between the upstream surface 132 of the occluder and the upper stop member 147.

As soon as the pumping stroke of the ventricle ceases for a valve in the aortic position, the back pressure flow lifts the occluder 125 so that the lower surface of the notch 139 contacts the arcuate surface 149b of the pivot post and the upstream surface 132 contacts a curved surface 155 formed on the stop 147 at a location intermediate of the upstream and downstream surfaces 149a,b of the pivot post 143, both of which surfaces 149b guide the pivoting motion. As pivoting movement continues to an intermediate position, the transitional edge surface 138 of the occluder essentially wipes along the curved undersurface 150 of the protrusion. When the occluder 125 reaches the fully closed position (see broken line illustration "A" in FIG. 14), its major and minor arcuate edges are in contact with the pair of generally semi-elliptical seats 161,163 which are formed as a part of the annular body 123 projecting inward from its interior surface. Because each of these seats is shaped with a generally conical or oblique configuration, the occluder will be self-centering so long as there is clearance at the notches 139, and there will be line contact between each edge of the occluder and one of the seat surfaces, thus providing a more positive seal around the periphery of the occluder when the heart valve is in the closed position. This unique self-centering seating feature is applicable to other heart valve designs where a pair of opposed seats can be provided, each of which has a surface that is a portion of generally the surface of a frustum of a cone, one being conical upward and the other being conical downward.

When the ventricle again begins to contract to resume the next pumping stroke, the pressure against the upstream surface 132 causes pivoting to begin, and the flow of blood displaces the occluder 125 slightly downstream so that the upper edge of the notch is in contact with the upper arcuate surface 149a of the pivot post which, along with a curved upper surface 157 formed on the lower stop 145 (also intermediate of the upstream and downstream surfaces 149a and 149b), defines the path of pivoting movement from the closed to the open position. An intermediate position is illustrated in full lines in FIG. 14, and the pivoting movement is terminated when the undersurface 133 of the occluder comes into contact with the stop surface 153 in the fully open position, as shown in broken line outline "B" in FIG. 14. In this position, there is excellent blood flow through the heart valve central passageway because, as best seen in FIG. 11, the post and stop arrangement only extends minimally into the passageway region and because the additional vacant area adjacent the surface 150 of the protrusion further decreases the resistance to flow through the valve.

As in the case of the bi-leaflet valve 21, the streamlined configuration provided by the integral post and stop means, as best seen perhaps in FIG. 10, provides a minimum of disruption to flow through the central passageway. Moreover, the integral construction allows one curved surface to be blended into the adjacent curved surface thus avoiding the creation of crevices and/or valleys that tend to permit stagnation and promote blood clotting.

Depicted in FIGS. 16–23 of the drawings is another alternative embodiment of a heart valve 221 which includes an annular body 223 designed to operate with a pair of flat occluders or leaflets 225. Generally, the same principles of design are executed in the heart valve 221 as were hereinbefore explained in detail with respect to the bi-leaflet valve 21, and therefore similar numbers in the 200 series are utilized to refer to comparable components. Moreover, it should be understood that, unless specifically stated hereinafter, the function and construction of the comparable components will be essentially the same as previously described.

The annular body 223 has an interior surface 227 which defines the passage or orifice through which the bloodstream will flow and is illustrated with a smooth exterior cylindrical surface 229 for the reason set forth hereinbefore. The interior surface 227 differs slightly from that of the bi-leaflet version shown in FIG. 1 in that the inwardly extending pivot arrangement is frustoconical instead of cylindrical.

A pair of leaflets 225 are used which are flat and have a uniform thickness throughout. Each leaflet 225 has a straight-edge portion 231, which as best seen in FIG. 17 is oriented at a suitable angle to the downstream surface 233 of the leaflet so that the two straight-edge portions 231 abut in substantially face-to-face contact when the pair of leaflets are in the closed position. Generally, the angle will be between about 110° and about 130° C., being of course dependent upon the orientation of the leaflets to the horizontal or transverse plane in the closed position. In addition, each of the leaflets 225 has a major arcuate, nearly semicircular, edge 235 (see FIG. 16) and a pair of intermediate of transitional straight edge portions 237 which are flat and perpendicular to the upstream and downstream surfaces of the leaflets. In addition, each leaflet 225 contains a pair of notches 239 disposed in its opposite lateral edges as defined by the straight edge surfaces 237. As best seen in FIG. 19, the notches are generally trapezoidal in shape; however, all of the defining edges are rounded as opposed to being sharp.

The passageway-defining interior surface 227 of the annular body 223 also has a right circular cylindrical shape for a major portion of its length but is interrupted by a pair of diametrically opposed flat sections 241 from which the support means for holding and defining the movement of the leaflets 225 radially project. The support means includes a pair of pivot posts 243, which are sized to fit within the notches 239 and which pivot posts are flanked by stop means 245, 247. As can be seen from FIGS. 18 and 23, the flanking stop means 245,247 project radially farther inward then do the pivot posts 243. Preferably, the pivot posts 243 and the flanking stop means are formed integrally with one another, and most preferably this overall support structure is formed as an integral part of the annular body 223. This can be accomplished by machining a pre-shaped body of pyrolytic carbon to final dimensions; however, it is preferably made using a specially prepared mandrel onto which pyrocarbon is deposited in a form similar to the final product. As best seen in FIG. 21, the pivot posts 243 each have a pair of opposite arcuate surface portions, a generally upper surface 249a and a generally lower surface 249b, which are sometimes referred to as lateral surface portions of the posts 243, so as to be distinguished from the flat end surface 251 of each pivot post, and which are frustoconical surfaces that are proportioned to interfit with the notches.

The leaflets 225 are suitably assembled with the annular ring 223 by suitably distorting the ring, as earlier set forth with respect to the FIG. 1 embodiment. In the assembled heart valve, the depth of the notch 239 is slightly greater than the length of the pivot post 243 so that one of the lateral edge surfaces 237 of each leaflet will bear against a facing flat section 241 of the annular body.

The closed position, depicted in FIG. 17, is substantially the same as in the valve shown in FIGS. 1–8; the arcuate edges 235 of the leaflets 225 lie in contact with the interior surface 227 of the annular body. Accordingly, the shape of the arcuate edge 235 will generally be that of a section of an ellipse, i.e., the intersection between a plane and a right circular cylinder, and the edge is preferably bevelled so as to more closely seat against the interior cylindrical surface. There may be line contact between the arcuate surface 255 of the stops 247 and the upstream surface 232 of the leaflets, and the straight-edge portions 231 of the two leaflets 225 will also abut in substantially face-to-face contact.

When the pumping stroke occurs, the pressure against the upstream surface of the leaflets 225 immediately displaces the leaflets downward against the central stop 245, and pivoting begins guided by the line contact between the undersurface 233 of the leaflets 225 and the curved surfaces 257. In addition, the leaflets will be displaced slightly so that there is contact between the upper surfaces of the notches 239 and the arcuate surfaces 249a on the pivot posts.

The integral pivot post and stop arrangement minimizes interference with blood flow, while at the same time providing for effective washing of the surfaces to avoid clotting as explained in respect of the heart valve 21. The movement of the leaflet about the surface 257 as a fulcrum is also primarily a rolling action, with a minimum of sliding movement, which is important to reduce wear. The blending of the integral pivot posts into the stop means allows the design to take advantage of the contact between the pivot post and the stop means and provides overall strength without having to precisely match individually machined components.

Depicted in FIGS. 24–30 of the drawings is another alternative embodiment of a heart valve 321 which includes an annular body 323 designed to operate with a pair of curved occluders or leaflets 325. Generally, the same principles of design are executed in the heart valve 321 as were hereinbefore explained in detail with respect to the bi-leaflet valve 21, and therefore similar numbers in the 300 series are utilized to refer to comparable components. Moreover, it should be understood that, unless specifically stated hereinafter, the function and construction of the comparable components will be essentially the same as previously described.

The annular body 323 has an interior surface 327 which defines the passage or orifice through which the bloodstream will flow and is illustrated with a smooth exterior cylindrical surface 329 for the reason set forth hereinbefore. The interior surface 327 differs slightly from that of the bi-leaflet version shown in FIG. 1 in that the inwardly extending pivot arrangement is spherical instead of cylindrical.

A pair of leaflets 325 are used which have a uniform thickness throughout but which are curved so as to preferably constitute a section of a hollow right circular cylinder, the axis of which is parallel to the pivot axis of the leaflet. Each leaflet 325 has a straight-edge 331, which as best seen in FIG. 26 is oriented at a suitable angle to the downstream surface 333 of the leaflet so that the two straight-edges 331 abut in substantially face-to-face contact when the pair of leaflets are in the closed position. Generally, the angle will be between about 110° and about 130°, being of course dependent upon the orientation of the leaflets to the horizontal or transverse plane in the closed position. In addition, each of the leaflets 325 has a major arcuate, nearly semicircular, edge 335 (see FIG. 24) and a pair of intermediate or transitional straight edge portions 337 which are flat and lie in a plane perpendicular to the straight-edges 331 of the leaflets. In addition, each leaflet 325 contains a pair of notches 339 disposed in its opposite lateral edges as defined by the straight edge surfaces 337. As best seen in FIG. 29, the notches are generally spherical in shape, and all of the defining edges are rounded as opposed to being sharp.

The passageway-defining interior surface 327 of the annular body 323 also has a right circular cylindrical shape for a major portion of its length but is interrupted by a pair of diametrically opposed flat sections 341 from which the support means for holding and defining the movement of the leaflets 325 radially project. The support means includes two pair of pivot posts 343, which are sized to fit within the notches 339 and which pivot posts are flanked by stop means 345, 347. As can be seen from FIG. 27, the flanking stop means 345,347 project radially farther inward than do the pivot posts 343. Preferably, the pivot posts 343 and the flanking stop means are formed integrally with one another, and most preferably this overall support structure is formed as an integral part of the entire annular body 323 by depositing pyrolytic carbon upon a suitably shaped mandrel as mentioned hereinbefore. As best seen in FIG. 28, each of the pivot posts 343 has an arcuate surface which is a section of a sphere. For functional purposes, these are referred to as a generally upper surface portion 349a and a generally lower surface portion 349b, the post 343 surface portions being proportioned to interfit with the notches.

The leaflets 325 are suitably assembled with the annular ring 323 by suitably distorting the ring, as earlier set forth with respect to the FIG. 1 embodiment. In the assembled heart valve, the depth of the notch 339 is slightly greater than the height of the pivot post 343 so that one of the lateral edge surfaces 337 of each leaflet will bear against a facing flat section 341 of the annular body.

The closed position, depicted in FIG. 26, is substantially the same as in the valve shown in FIGS. 1-8, and the arcuate edges 335 of the leaflets 325 lie in contact with the interior surface 327 of the annular body. Accordingly, the shape of the arcuate edge 335 will generally be that of a section of an ellipse, i.e., the intersection between a plane and a right circular cylinder, and the edge is preferably bevelled so as to more closely seat against the interior cylindrical surface. There may be line contact between the arcuate surface 355 of the stops 347 and the upstream surface 332 of the leaflets, and the straight-edge portions 331 of the two leaflets 325 will also abut in substantially face-to-face contact.

When the pumping stroke occurs, the pressure against the upstream surface of each leaflet 325 immediately displaces the leaflets downward against the central stop 345, and pivoting begins guided by the line contact between the undersurface 333 of the leaflets 325 and the curved surfaces 357. In addition, the leaflets will be displaced slightly so that there is contact between the upper surfaces of the notches 339 and the arcuate surfaces 349a on the pivot posts.

The integral pivot post and stop arrangement minimizes interference with blood flow, while at the same time providing for effective washing of the surfaces to avoid clotting as explained in respect of the heart valve 21. The movement of the curved leaflet about the surface 357 as a fulcrum is primarily a rolling action, with a minimum of sliding movement, and reduces wear. The curved surface effect of the leaflets in the open position is felt, as a result of the venturi-like central passageway design, to advantageously reduce resistance to blood flow in this region and may enhance overall performance.

Although the invention has been described with regard to two preferred embodiments, it should be understood that various changes and modifications as would be obvious to one having the ordinary skill in this art may be made without departing from the scope of the invention which is defined by the claims appended hereto. For example, with respect to many of the novel features of the invention, the occluders which are shown in various of the embodiments need not be flat but could be curved in cross-section, as have been shown in the heart valve design depicted in FIGS. 24 to 30.

Particular features of the invention are emphasized in the claims that follow.

What is claimed is:

1. A heart valve prosthesis comprising
a generally annular body which has an interior surface that defines a central passageway for blood flow therethrough,
occluder means supported on said body for alternately blocking and then allowing the flow of blood through said passageway in a predetermined direction,
said occluder means having upstream and downstream major surfaces and being formed with aligned notch means at opposite locations in the periphery thereof,
a pair of aligned pivot posts projecting generally radially inward from said interior surface of said body, which posts have arcuate convex opposite lateral surfaces and are receivable within said notch means, and
stop means projecting inward from said interior surface at locations generally flanking each of said pivot posts and extending radially farther inward than said pivot posts, said stop means presenting a pair of curved surfaces in regions adjacent to said pivot posts and overlying major surfaces of said occluder means, each of which curved surfaces lies in a region located intermediate of said opposite arcuate convex side surfaces of said post and extends radially inward thereof so as to provide a pair of oppositely disposed fulcrums that face each other, flanking said pivot posts,
said posts being proportioned to be received in said notch means so as to allow at least some nonrotational displacement of said occluder means away from one of said curved surfaces toward the other of said curved surfaces whereby supporting contact is alternated between respective curved surfaces and occluder means major surfaces as said occluder means repeatedly open and close.

2. The prosthesis of claim 1 wherein said stop means is formed integrally with said pivot posts.

3. The prosthesis of claim 2 wheren said stop means curved surfaces are blended into said pivot post arcuate surface portions.

4. The prosthesis of claim 3 wherein said stop means and said pivot posts are integral with said annular body.

5. The prosthesis of claim 2 wherein the focal point of each of said convex surfaces of said pivot posts is located past the center point of said pivot posts.

6. The prosthesis of claim 1 wherein said arcuate surface portions are cylindrical surface portions.

7. The prosthesis of claim 1 wherein said arcuate surface portions are frustoconical surface portions.

8. The prosthesis of claim 1 wherein said arcuate surface portions are spherical surface portions.

9. The prosthesis of claim 1 wherein said occluder means is a single disc having a pair of opposite straight peripheral segments wherein said notch means are respectively located which are spaced apart a distance less than the diameter of the generally circular cross section central passageway.

10. The prosthesis of claim 9 wherein said pivot post and said stops project from a pair of protrusions that lie mainly on one side of a diameter of said passageway so that said occluder has a major peripheral section that is generally semicircular and a minor arcuate section that is substantially shorter and that terminates at said pair of opposite straight peripheral segments, which in turn terminate in a pair of segments perpendicular thereto which are collinear and interconnect with the ends of said major peripheral section.

11. The prosthesis of claim 10 wherein each of said protrusions includes a generally downstream-facing curved surface adjacent which one of said perpendicular segments moves during opening and closing movement of said occluder.

12. The prosthesis of claim 1 wherein said occluder means includes a pair of generally semicircular or semi-elliptical discs, each of which has a periphery which includes a straight edge section, a major arcuate edge section, and a pair of generally diametrically opposite straight segments wherein said notch means are respectively located.

13. A heart valve prosthesis comprising
a generally annular body which has an interior surface that defines a central passageway for blood flow therethrough,
a pair of occluders supported on said body for alternately blocking and then allowing the flow of blood through said passageway in a predetermined direction,
said occluders each having upstream and downstream major surfaces and being formed with aligned notch means at opposite locations in the periphery thereof,
two pairs of aligned pivot posts projecting generally radially inward from said interior surface of said body, which posts each have arcuate convex upstream and downstream surfaces and are receivable within said notch means, and
stop means projecting inward from said interior surface at locations generally flanking each of said pivot posts and extending radially farther inward than said pivot posts, said stop means presenting a pair of curved surfaces in regions adjacent to said pivot posts and overlying respective major surfaces of said occluder means, each of which curved surfaces lies in a region located intermediate of said arcuate convex surfaces of said post and extends radially inward thereof so as to provide a pair of oppositely disposed fulcrums adjacent each pivot post that face each other, flanking said pivot posts, said posts being proportioned to be received in said notch means so as to allow at least some nonrotational displacement of said occluder means away from one of said curved surfaces toward the other of said curved surfaces whereby supporting contact is alternated between respective curved surfaces and occluder means major surfaces as said occluder means repeatedly open and close.

14. The prosthesis of claim 13 wherein said stop means curved surfaces are blended into said pivot post arcuate surface portions and said stop means and said pivot posts are integral with said annular body.

15. The prosthesis of claim 13 wherein each of said occluders is a generally semicircular disc the periphery of which includes a straight edge section, a major arcuate edge section, and a pair of straight segments wherein said notch means are respectively located, said disc being curved so as to generally constitute a section of a hollow right circular cylinder the axis of which is parallel to the pivot axes defined by said aligned pairs of pivot posts.

* * * * *